US006686299B2

(12) United States Patent
Montemagno et al.

(10) Patent No.: US 6,686,299 B2
(45) Date of Patent: Feb. 3, 2004

(54) NANOSYRINGE ARRAY AND METHOD

(76) Inventors: Carlo D. Montemagno, 15245 Mulholland Dr., Los Angeles, CA (US) 90077; Hercules Neves, 12041 River Grove Ct., Moorpark, CA (US) 93021

( * ) Notice: Subject to any disclaimer, the term of this patent is extended or adjusted under 35 U.S.C. 154(b) by 0 days.

(21) Appl. No.: 10/178,056

(22) Filed: Jun. 21, 2002

(65) Prior Publication Data

US 2003/0015807 A1 Jan. 23, 2003

Related U.S. Application Data

(60) Provisional application No. 60/300,013, filed on Jun. 21, 2001.

(51) Int. Cl.[7] ............................................. H01L 21/00
(52) U.S. Cl. ..................................................... 438/800
(58) Field of Search .................... 438/800; 257/798; 604/68, 891.1, 892.1

(56) References Cited

U.S. PATENT DOCUMENTS 6,489,629 B1 * 12/2002 Eriguchi et al. .............. 257/14

2003/0010971 A1 * 1/2003 Zhang et al. .................. 257/15

FOREIGN PATENT DOCUMENTS

| EP | 000892444 A2 * | 11/1994 | .......... H01L/33/00 |
| WO | WO 00/74764 A1 * | 12/2000 | .......... A61M/37/00 |

* cited by examiner

*Primary Examiner*—Craig A. Thompson
*Assistant Examiner*—David S Blum
(74) *Attorney, Agent, or Firm*—Schwegman, Lundberg, Woessner & Kluth, P.A.

(57) ABSTRACT

A nanosyringe is constructed using micro fabrication and nano fabrication techniques on a silicon substrate. The nanosyringe includes a membrane of silicon carbide. The position and operation of individual nanosyringes, arranged in an array of nanosyringes, can be independently controlled. A nanosyringe array can inject or extract a fluid from one or more cells or other structures. Microfluidic structures coupled to the nanosyringe allow external pumping or extraction. A cell matrix or organelles of individual cells can be non-destructively sampled in real time.

10 Claims, 7 Drawing Sheets

NANOSYRINGE ARRAY AND METHOD

RELATED APPLICATION

This document claims priority to related provisional patent application serial No. 60/300,013, filed on Jun. 21, 2001 and titled NANO SYRINGE ARRAY AND METHOD, herein incorporated by reference.

FIELD OF THE INVENTION

The present invention relates to nanosyringes, and in particular to a nanosyringe array and method of making the nanosyringe array.

BACKGROUND

Microinjection techniques have been used for a variety of applications, including high-efficiency transformation, protein injection, pathogen injection and organelle transfer. Transfer of DNA to mammalian cell cultures and embryos using microinjection has also been performed. More recently, microinjection has been employed to develop transgenic animals for pharmacological studies in the cardiovascular system, endocrine system, cancer and toxicology. It has also been used to examine the role of the c-fos gene as a mitogenic signal in mammalian cells by injection of protein inhibitors and monoclonal antibodies that block mitogenic activities.

Micropipettes are primarily constructed of tapered borosilicate glass, quartz, or aluminosilicate needles with a minimum diameter of between 50 and 100 nm. The primary disadvantages of these pipettes include inherent damage inflicted on host cells, the inability to accurately control injection rates, the inability to inject more than one cell at a time, and the inability to inject more than one sample into a given cell at one time. Recently, a galinstan expansion femtosyringe was formed that reduced the damage inflicted on host cells. In addition, heat induced galinstan (also known as gallinstan, a liquid metal alloy of gallium, indium and tin) was used to accurately control the rate of injection. These femtosyringes permit the injection of subcellular organelles such as vacuoles, mitochondria and chloroplasts while maintaining the integrity of cell membranes. Such femtosyringes are expensive to form, and do not facilitate the injection of more than one cell at a time, nor do they provide the ability to inject different substances simultaneously into the same cell. Expensive needle puller equipment is also required to form femtosyringes.

In one attempt to provide an array of microneedles, a plurality of parallel hollow non-silicon microneedles are formed on a planar surface of a substrate. Multiple arrays of these needles can be coupled to form a three dimensional array with the substrates still attached, or removed. Cross coupling channels provide for free fluid flow. The array is used to increase the flow rate of a fluid to be injected. Further, the size of the needles constructed using this technique are much larger than those required to permit the injection of subcellular organelles, and may lead to unacceptable damage to cellular structures.

SUMMARY

A nanosyringe is constructed using micro and nano fabrication techniques on a substrate. In one embodiment, the nanosyringe is formed as a membrane of silicon carbide or silicon nitride on a silicon substrate using photolithography or other means. The nanosyringe comprises a tip for penetrating a host without destroying the integrity of a host membrane. As used herein, the term needle is interchangeable with the term syringe.

In one embodiment, an array of nanosyringes comprises a large number of independently controlled nanosyringes suitable for injecting a large number of cells or other structures at a given time, or injecting a variety of samples into a single cell at one time or at staggered time intervals. In one embodiment, each nanosyringe is independently controlled with respect to injection properties. The spacing of the nanosyringes is adjusted based upon a specific objective at the time of formation of the array. For example, arrays with a large spacing of 5–10 μm may be used for injecting large numbers of cells. As another example, arrays with smaller spacing, such as less than 50 nm between tips, may be used for injection various samples into a single cell at specific rates, time intervals and location. They are further used to increase the flow rate of a sample to a cell. In one embodiment, a variety of samples can be injected in varying amounts and at varying times.

In one embodiment, the arrays are utilized to draw fluid or remove samples from cells. An external pumping system coupled to one or more nanosyringes allows non-destructive sampling of a cell matrix or organelles of a cell as well as real time sampling and analysis of physiological changes within an individual cell. In one embodiment, a nanosyringe both injects a first fluid and extracts a second fluid coincident with a single penetration of a host membrane.

In one embodiment, sensor and detection capabilities, as well as micro-pumps and valves are directly integrated into the system using micro and nano fabrication techniques on a semiconductor substrate. This provides the ability to instantaneously sample a cell's cytoplasm following the addition of a particular drug injected into the nucleus of that cell. Arrays of nanosyringes are also formed for a variety of microfluidic systems where precise delivery of liquids is desired. In one embodiment, a system is provided to independently position individual nanosyringes within a three axis coordinate system.

In one embodiment, a silicon carbide nanosyringe is constructed using micro and nano fabrication techniques on a silicon substrate. Each nanosyringe is independently controlled with respect to injection properties. An external pump system coupled to a nanosyringe array allows non-destructive sampling of the cell's matrix and organelles, and real time sampling and analysis of physiological changes within individual cells. Sensor and detection capabilities, as well as micro-pumps and valves are directly integrated into the system using micro and nano fabrication techniques on a semiconductor substrate.

The present subject matter includes fabrication of thin, suspended membranes supported by a silicon substrate. In various embodiments, the membrane includes thin film materials such as silicon nitride or silicon carbide. In one embodiment, the membrane is formed using a non-planar (that is, not flat) surface. The present subject matter includes membranes formed using a cylinder, column or cone.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
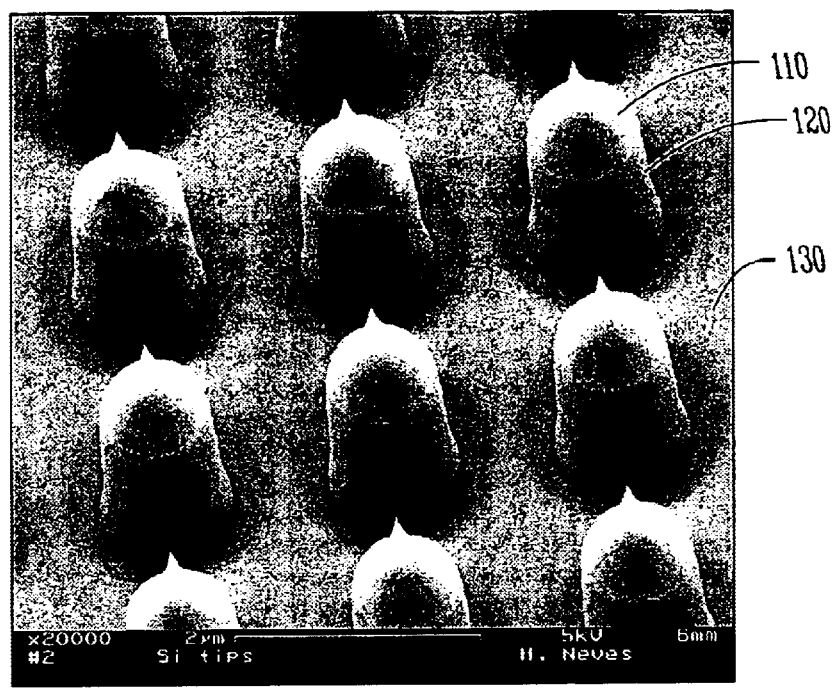
FIG. 1 illustrates a scanning electron microscope micrograph of an array of silicon tips used to form nanosyringes.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

In various embodiments, the present subject relates to a stationary nanosyringe, an array of self-aligned stationary nanosyringes and an array of individually positionable nanosyringes.

A method of making a nanosyringe or nanosyringe array includes forming at least one silicon tip as shown at 110 in FIG. 1. In one embodiment, the tips are atomically sharp. An array of silicon tips is shown in FIG. 1. The silicon tips 110 serve as a sacrificial material for syringe fabrication. The tips 110 shown in FIG. 1 are less than approximately 10 nm in diameter, and each has a shaft 120 which is approximately 1 μm in diameter. These sizes referred to are merely one example. Other sizes, as well as materials other than silicon, are well within the scope of the invention as will be apparent from a description of the process steps used to form the tips.

Silicon wafer 130 is initially oxidized at 1100° C. in a steam ambient to form a layer of silicon dioxide. A pattern of dots approximately 500 nm in diameter are defined through a lithographic process, such as photolithography using an i-line stepper. The pattern is transferred onto the silicon dioxide layer through fluorine-based reactive ion etching (RIE). This is followed by chlorine-based inductively coupled plasma (ICP) RIE to transfer the pattern onto the silicon substrate, resulting in an array of dots.

The silicon layer is again oxidized. Localized stress effects acting around the neck of the post or cylinder produces an atomically sharp tip. Reactive ion etching is used again to remove the oxide from the floor of the silicon layer. Then another chlorine RIE is performed to further etch the silicon and create the shaft 120 for each tip 110. The silicon dioxide is removed using a 1:6 buffered hydrofluoric acid solution. Methods other than those described herein can be used to wholly or partially remove the silicon substrate.

Figure 2:
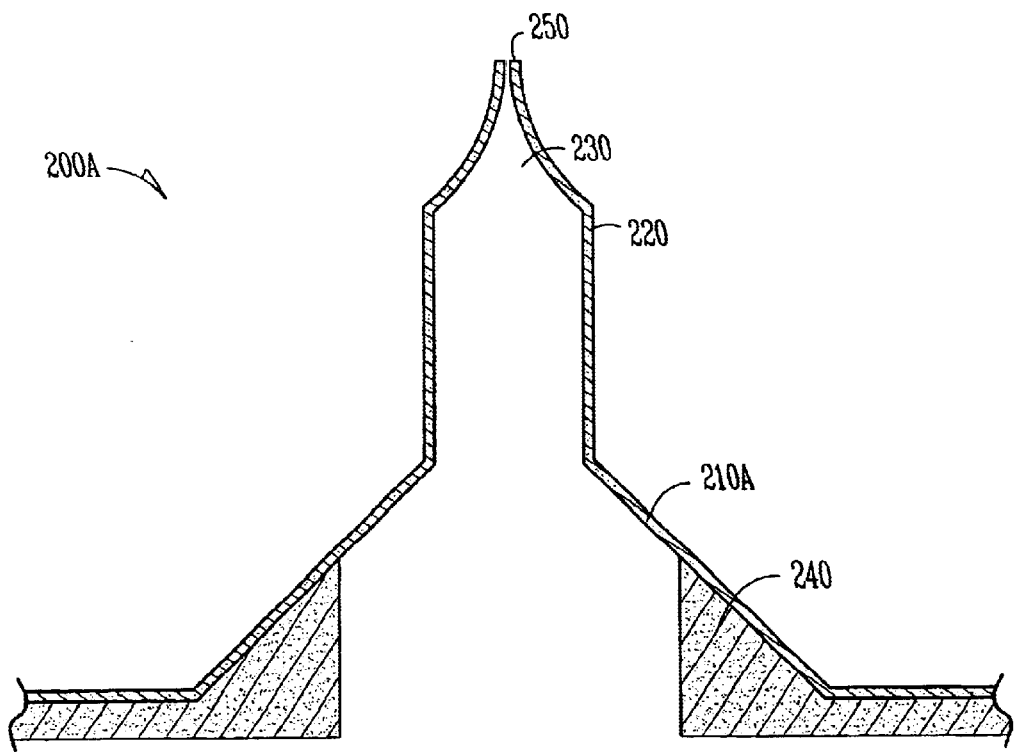
FIG. 2 illustrates a cross section of a nanosyringe.

In one embodiment, a faceted profile or pedestal at the base of the shaft is formed by anisotropic wet etching. For example, using (100) silicon, an anisotropic wet etchant such as potassium hydroxide yields <111> cuts at an angle of 54.74° relative to the surface of the silicon substrate. The cut is illustrated in FIG. 2 at 210A, which shows a cross section of a finished nanosyringe indicated generally at 200A.

The angle of the cut is determined, in part, by the orientation of the crystal planes of the silicon substrate. The orientation of the crystal planes are expressed using Miller indexes and relate to how the silicon crystal is sliced. Wet anisotropic etching will etch the silicon at different rates depending on the orientation of the crystal planes.

The membrane is next fabricated on the silicon tip, shaft and faceted base followed, in one embodiment, by removal of the silicon structure by a combination of wet and dry etching steps. Selective removal of the silicon can result in structural supporting members within or about the nanosyringe.

Figure 3:
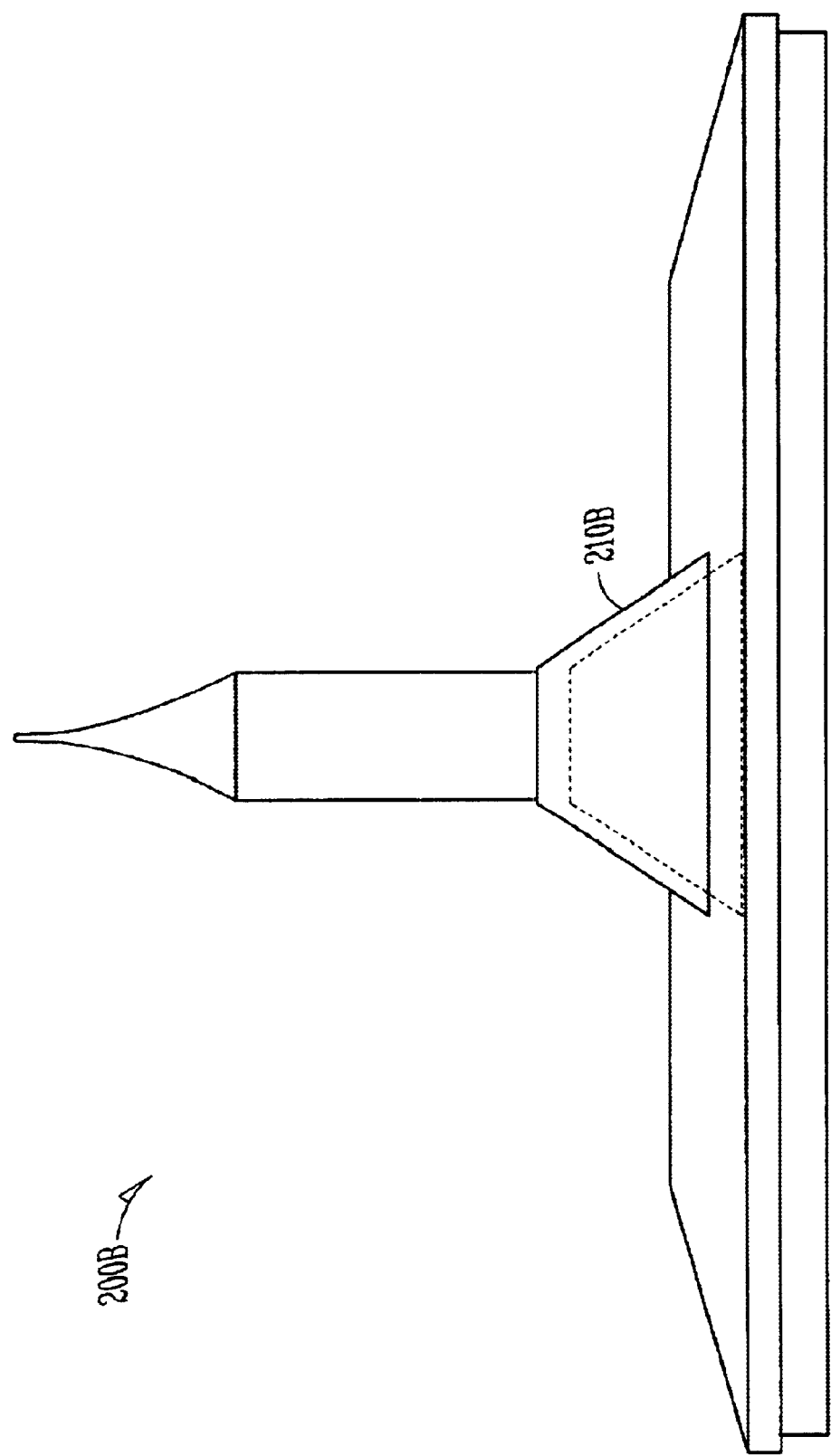
FIG. 3 illustrates a perspective view of the nanosyringe of FIG. 1.

FIG. 3 provides a perspective of a nanosyringe. To obtain the finished nanosyringe, the previously formed silicon tip is coated with a conformal membrane material 220 such as silicon nitride or silicon carbide. A portion of the silicon tip is removed through a combination of wet and dry RIE etching to leave a core open area, or syringe cavity, 230 for fluid flow. The syringe cavities are connected in one embodiment to channels and reservoirs for fluid dispensing. A base structural support area 240 remains following the etching to provide support for the syringe membrane material 220.

An opening, or nozzle, at the tip of the syringe 250 is formed using a process similar to submicron nozzle fabrication. In one embodiment, a polymer layer or other photoresist material is used as an etch mask. The tip may be etched using traditional etching methods.

In one embodiment, a localized stress effect can be used to form a syringe nozzle. In this embodiment, a concentration of stresses occurring within the membrane at a sharp radius portion of the silicon nitride causes a fracture which forms a nozzle on the syringe. The sharp, or small, radius portion of the membrane separates from a larger radius portion.

In one embodiment, silicon carbide or other material is etched back to form a syringe nozzle. In one embodiment, greater uniformity in nozzle placement and dimension is achieved by an etching process.

In one embodiment, low-pressure chemical vapor deposition (LPCVD) is used to deposit the membrane on the silicon tip. In one embodiment, LPCVD is used to deposit silicon nitride and localized stresses are controlled by introduction of controlled amounts of oxygen in the film (or membrane) during deposition, thus forming silicon oxynitride.

In general, LPCVD provides a membrane pin-hole free and with uniform physical properties. Stresses induced are generally characterized as tensile and the range of levels stress tends to be rather narrow.

In one embodiment, the process of membrane fabrication includes plasma enhanced chemical vapor deposition (PECVD). As with LPCVD, the deposited film is determined by a chemical reaction between the source gases supplied to the reactor. Since the resulting films are non-stoichiometric, a wide range of stress values can be obtained, from tensile stress to compressive.

In one embodiment, the silicon surface of the tips is converted to silicon carbide (SiC) by carbonization. Silicon carbide conformally coats the silicon tip and when carbonized, the membrane provides a sharper and stronger nanosyringe.

In one embodiment, the nanosyringe remains stationary and a cell is moved into position such as by using a microelectromechanical systems (MEMS) actuator driven stage. In one embodiment, the cell is positioned using laser tweezers.

Figure 4:
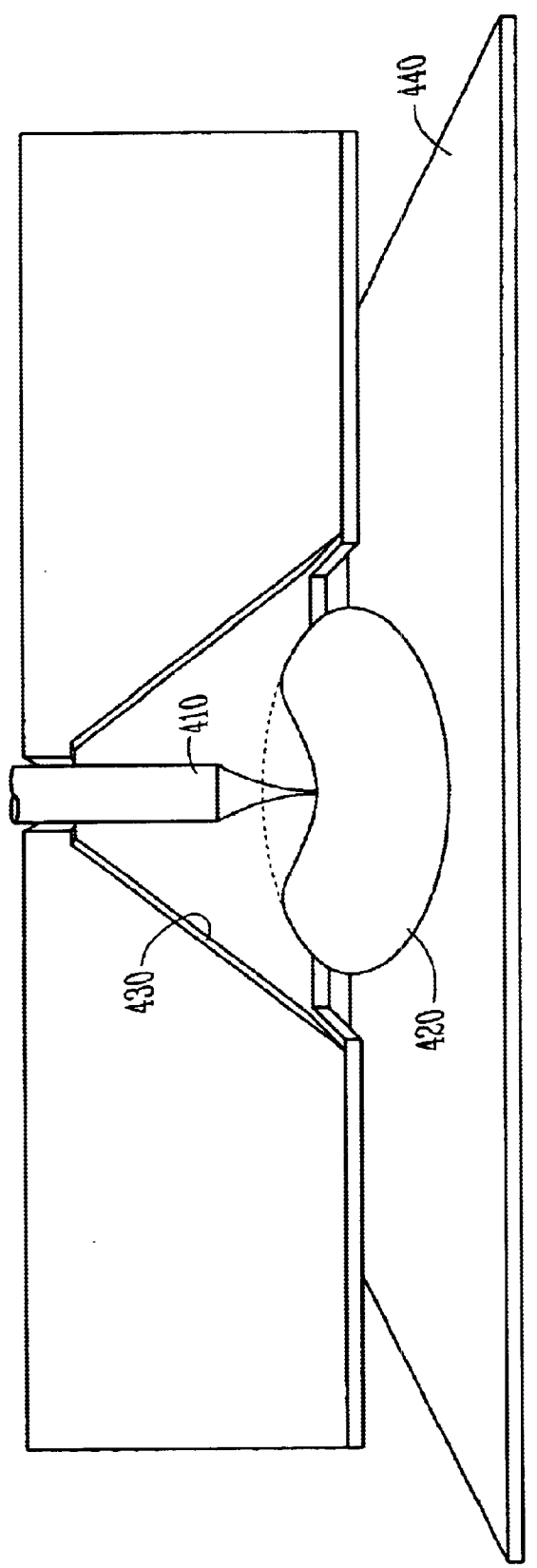
FIG. 4 illustrates a perspective partial section view of a self-aligned nanosyringe.

FIG. 4 shows nanosyringe 410 adapted for penetrating cell 420. A faceted cavity 430 is formed in the same manner as the faceted pedestal in FIG. 2 using an anisotropic etch in place of the chlorine RIE to remove silicon to form the shaft of the syringe. Faceted cavity 430 is used to trap and position the cell at the same time. In one embodiment, cell 420 is supported by flat quartz slide 430. Syringe 410 is self-aligned within faceted cavity 430. In addition to, or in lieu of, the faceted cavity, other structure may be formed in the silicon substrate to capture cell 420. For example, conical structures or posts may be used to position cell 420 for penetration by nanosyringe 410.

Figure 5:
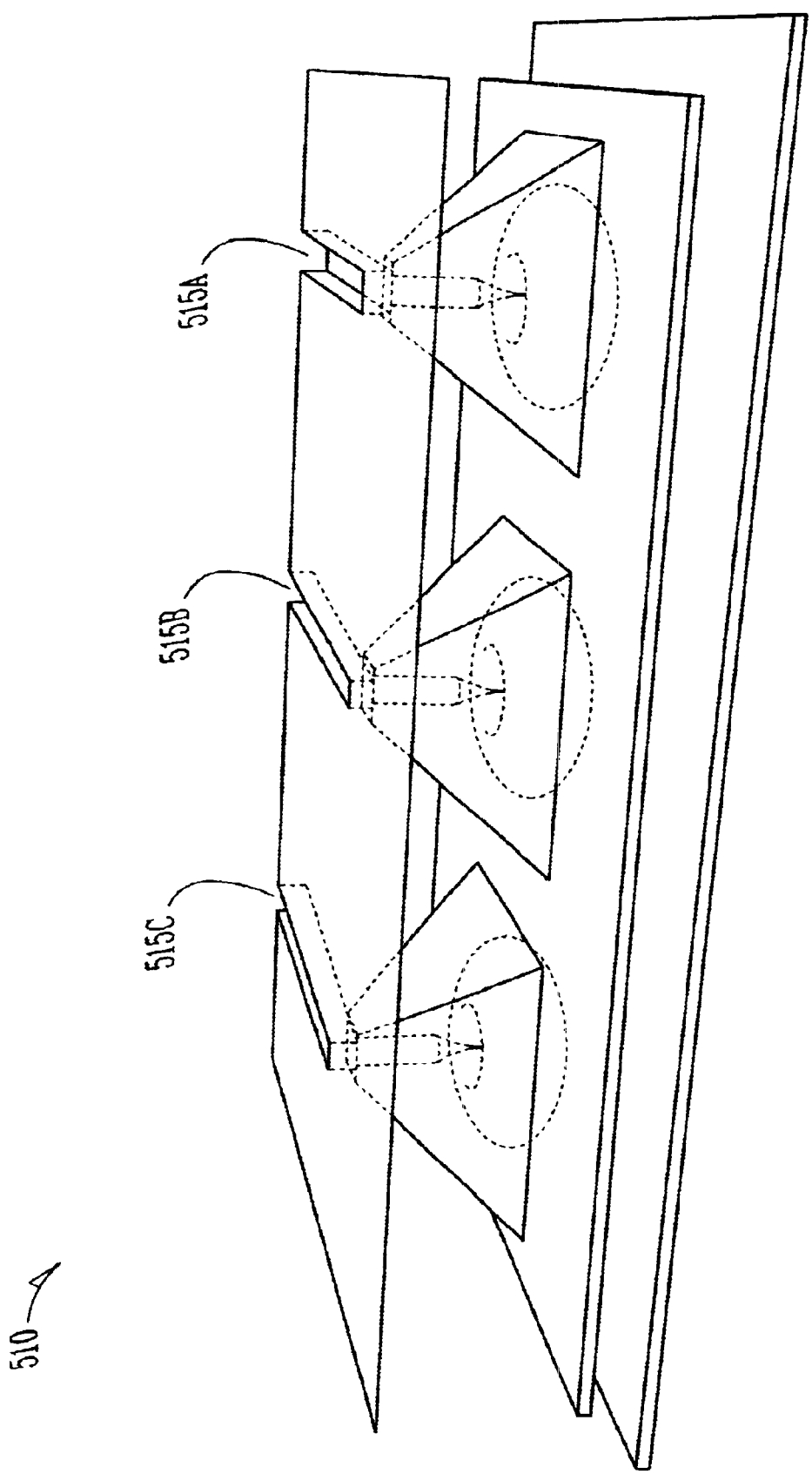
FIG. 5 illustrates a perspective partial section view of an array of self-aligned nanosyringes.

In one embodiment, quartz slide 430 comprises a cell culture, an array of syringes, each having a faceted cavity, is lowered against the cell culture to trap and hold cells in place in a position reachable by the syringes as shown 510 in FIG. 5. In one embodiment, a channel for each syringe is provided in a backside of the substrate at 515A, 515B and 515C. As previously indicated, each channel provides an independent path to a reservoir. The paths may be connected in some embodiments so that more than one syringe is coupled to the same reservoir, or multiple channels and syringes may have separate reservoirs. In further embodiments, more than one syringe is formed within a faceted cavity to facilitate the injection of multiple samples or substrates into a particular cell at a specific time or time intervals.

Patterning the backside of the silicon wafer includes leaving some silicon to make channels, pumps, and other structures for coupling to other systems for fluid handling.

For example, in one embodiment, a fluid reservoir is patterned into the silicon. The reservoir receives fluid by capillary extraction or contains fluids for delivery using the nanosyringe.

Figure 6:
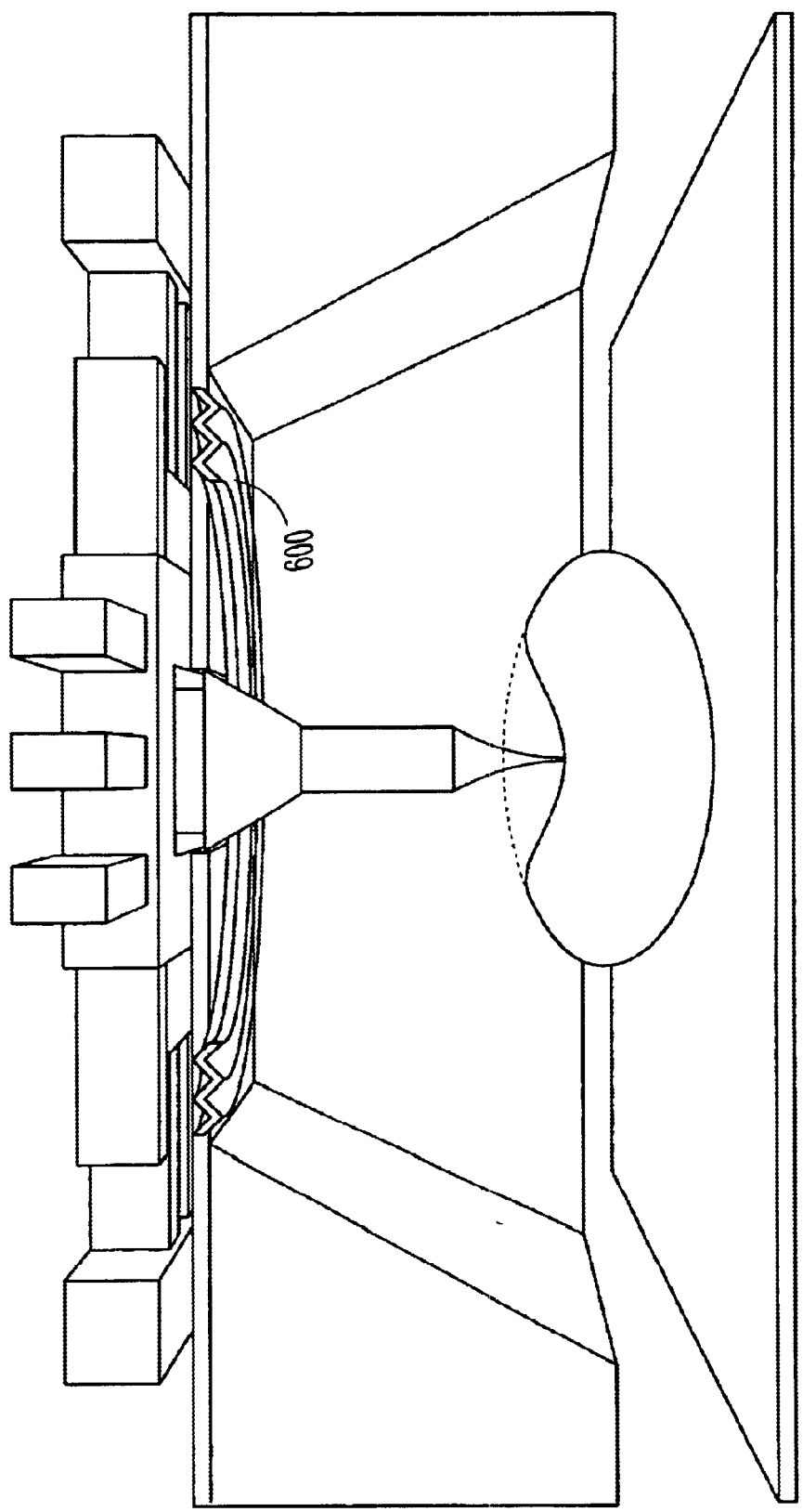
FIG. 6 illustrates a view of a positionable nanosyringe relative to a silicon substrate.

FIG. 6 illustrates a positionable nanosyringe adapted for movement relative to a silicon substrate. MEMS actuators (including electrostatic comb drives or piezo elements, for example) drive the syringe laterally in the x-axis and y-axis to precisely position the syringe with respect to the object to be injected.

In one embodiment, syringes and arrays are movable with respect to the cavity. Incorporation of a flexible structure or suspension mechanism for syringe displacement and inclusion of actuators for moving the syringe in a plane, as well as up and down, are utilized. In one embodiment, electrostatic actuators for x-axis and y-axis displacement are constructed using the remaining backside of the silicon substrate. In one embodiment, the electrostatic actuator includes one or more comb drive actuators. Out-of-plane z-axis motion is provided by similar actuators by means of electrostatic levitation. In one embodiment, corrugated structure 600 is disposed concentric to the syringe and acts as a bellows to allow freedom of movement of the syringe.

In one embodiment, both independent steering and a self-alignment faceted cavity are used with a particular nanosyringe.

Exemplary Embodiment

The following describes one embodiment of the present subject matter.

Figure 7A:
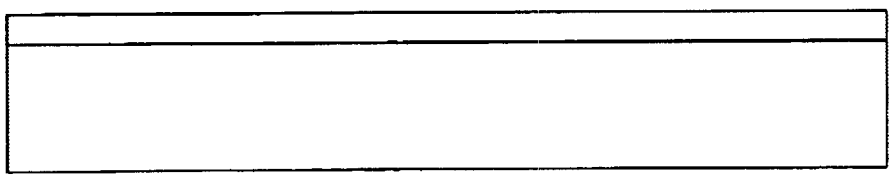
FIG. 7 depicts a method of fabricating a nanoneedle (or nanosyringe) array.
Figure 7B:
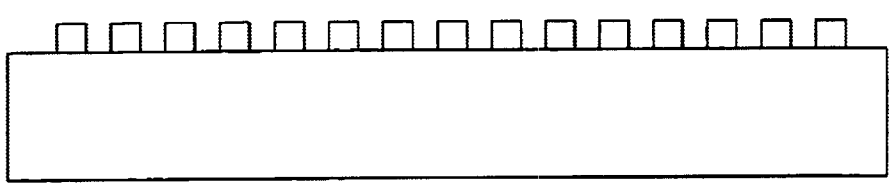
Figure 7C:
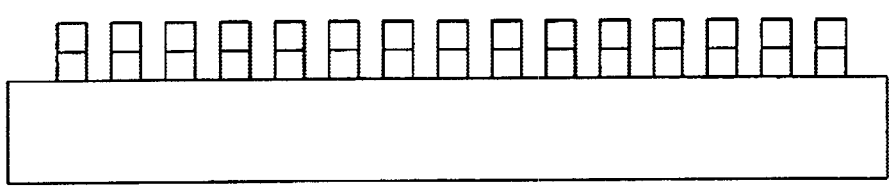
Figure 7D:
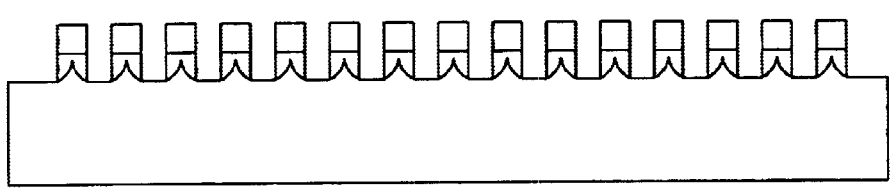
Figure 7E:
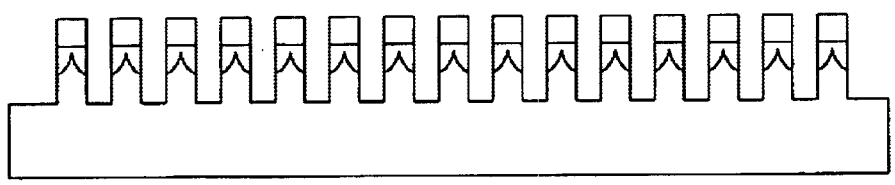
Figure 7F:
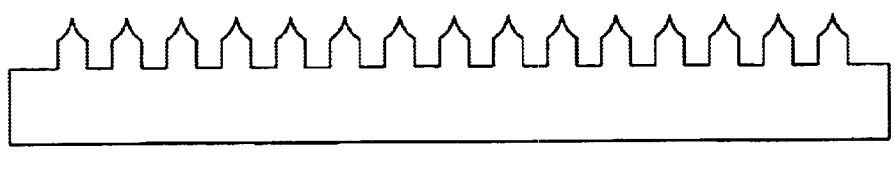

Standard <100> silicon wafers is used as the base material for the array fabrication. The individual fabrication steps are depicted in FIG. 7. Initially the wafers were thermally oxidized at 1100° C. in a steam ambient with trichlorethane (TCA) to form a 0.7-$\mu$m thick layer of $SiO_2$ (FIG. 7A). The wafers were then primed at 90° C. in hexamethyldisilazane (HMDS) vapor to promote photoresist adhesion, followed by photoresist coating. A photolithography step was performed using a 10× i-line step-and-repeat system to form an array of 0.5 $\mu$m dots. The dot pattern is then transferred onto the silicon dioxide layer by magnetron-assisted reactive ion etch, using $CHF_3$ (30 sccm) at 1 kW until the open areas were free of This patterned silicon dioxide (FIG. 7B) then serves as an etch mask to etch the underlying silicon to define standing silicon posts. The posts were etched using a chlorine-based inductively coupled plasma ($Cl_2$=50 sccm, $BCl_3$=2.5 sccm, ICP power=75 W) to obtain 1-$\mu$m tall silicon posts (FIG. 7C). A second thermal oxidation step is performed to turn these silicon posts into atomically sharp tips. When the posts are thermally oxidized, a stress effect around the base of the post causes an uneven oxidation along the length of the post thus resulting in a cone-like structure. This was performed in a steam ambient, with TCA added, at 1100° C., for about 30 minutes (FIG. 7D). The initial oxide which remained on top of the tips can then be used as an etch mask to define a shaft at the base of the tips. To do this, a plasma etchback step is performed in $CHF_3$ ambient to strip the oxide surrounding the tips. This is followed by a chlorine ICP etch step to define the shafts (FIG. 7E). The samples are then immersed in a 1:6 buffered hydrofluoric acid solution to strip all the remaining oxide, thus exposing the tips (FIG. 7F). FIG. 1 illustrates a typical silicon tip array obtained by this process.

Figure 7G:
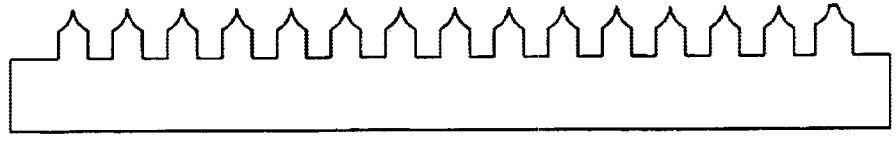
Figure 7H:

Subsequent steps form the needles. By way of overview, the needles are formed by a suspended silicon nitride membrane utilizing the tip array as a mold. Suspended silicon nitride membranes are formed into a corrugated membrane, which conforms to the shape of the tips. The samples are coated with a layer of low-stress $Si_3N_4$ using low-pressure chemical vapor deposition (LPCVD) as shown in FIG. 7G. The thickness of this layer depends on the needle diameter and aperture desired. Photolithography is performed on the backside of the wafers using an infrared aligner. This defines the windows for the through-wafer etch. The wafers are then immersed in a 50% wt. potassium hydroxide solution at 90° C. until the cores of the tips are removed.

Figure 8:
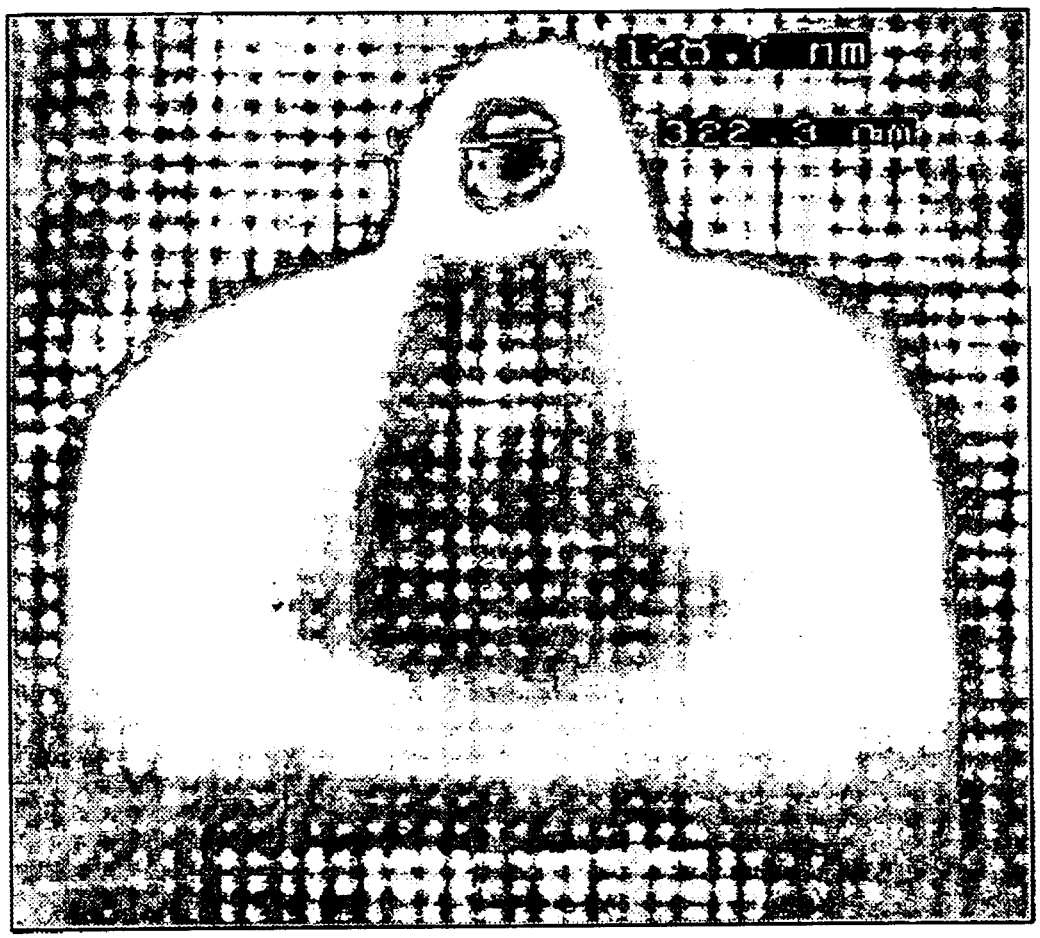
FIG. 8 illustrates a scanning electron micrograph of a $Si_3N_4$ needle.

The needle apertures are created using a process similar to submicron nozzle fabrication. In one embodiment, photoresist is spun to completely cover the needles and an RIE etchback is performed. FIG. 8 shows a completed needle.

Additional Embodiments

In one embodiment, materials other than silicon and silicon carbide are used for fabrication of a nanosyringe. For example, thin metal films deposited using techniques such as, but not limited to, chemical vapor deposition, physical vapor deposition, electroplating, and electroless plating.

In one embodiment, a nanofabricated array of syringes is adapted for transcutaneous injection of medicament or for drawing blood or cell samples. In such an embodiment, a plurality of nanosyringes, each fabricated of silicon carbide, are arranged on a substrate having structural silicon reinforcement beams or members. The depth of penetration of a nanofabricated array of syringes may be sufficiently shallow to avoid disturbing nerve cells and therefore offers a low pain method of drawing samples or delivering medicine. The present subject matter may be used to inject fluids into blood cells or to extract cell matrix or organelles for further analysis.

In one embodiment, the nanosyringe structure is strengthened by providing reinforcing members on the silicon substrate. For example, in one embodiment, the silicon includes a network or grid of reinforcement beams etched or otherwise formed into the backside of the array or within the nanosyringe. In one embodiment, the nanosyringe is fabricated of a membrane material suited for a harsh environment.

In one embodiment, the methods and devices described herein are applied to the fabrication and use of syringes that are larger or smaller than nano scale dimensions. For example, in various embodiments, the syringes are more properly described as millisyringes, microsyringes, picosyringes or femtosyringes.

In one embodiment, one or more microfluidic devices or actuators are coupled to a nanosyringe. For example, in one embodiment, a flow valve is coupled to a nanosyringe. Other microfluidic devices are also contemplated, including, but not limited to pumps, reservoirs, sensors, fluid conduits or channels. In one embodiment, a microfluidic device or actuator is fabricated on the same silicon substrate as the nanosyringe. In one embodiment, the nanosyringe is fabricated on a first silicon substrate and a microfluidic device or actuator is fabricated on a second silicon substrate and the first and second substrate are subsequently bonded together.

In one embodiment, the membrane is fabricated of material other than silicon carbide. Silicon carbide exhibits robust performance in a harsh environment, has good mechanical hardness and is relatively chemically inert. Polycrystalline SiC can be deposited using PECVD. Also, 3C—SiC can be formed on silicon by carbonization of the silicon surface. In either case, thin conformal films can be directly deposited on silicon. Silicon can be used as a sacrificial member because of the high chemical selectivity between Si and SiC. The SiC film can be released by etching using wet chemistries such as potassium hydroxide, ethylene-diamine/pyrocatechol (EDP) or hydrofluoric acid. High selectivity is also found in reactive ion etching which also allows fabrication of mechanical supporting structures within the nanofabricated device.

In one embodiment, the nanosyringe or nanosyringe array is optically transparent. Transparency allows monitoring operation of the nanosyringe via an optical microscope.

In one embodiment, the tip is formed on the silicon substrate without a cylinder or shaft at the base. The membrane is formed on the tip as described above. In one embodiment, microfluidic devices or MEMS devices are coupled to the nanosyringe, also as described above.

CONCLUSION

The above description is intended to be illustrative, and not restrictive. Many other embodiments will be apparent to those of skill in the art upon reviewing the above description.

What is claimed is:

1. A method comprising:

forming a column on a silicon substrate;

depositing a membrane on the column;

removing a portion of the column after depositing the membrane; and fracturing a portion of the membrane to form a nozzle end.

2. The method of claim 1 wherein fracturing includes inducing stress in the membrane.

3. The method of claim 1 wherein forming the column includes forming a faceted base.

4. The method of claim 1 wherein forming the column includes forming a tip.

5. The method of claim 1 wherein forming the column includes performing anisotropic wet etching.

6. The method of claim 1 wherein removing the portion of the column includes performing reactive ion etching (RIE).

7. The method of claim 1 further comprising forming a flexible structure in the silicon substrate proximate the column.

8. The method of claim 7 wherein forming the flexible structure includes forming a corrugated surface.

9. The method of claim 7 further comprising coupling at least one mechanical actuator to the membrane.

10. The method of claim 1 further comprising forming a faceted cavity adapted for receiving a single cell.

\* \* \* \* \*